(12) United States Patent
Bekas et al.

(10) Patent No.: US 10,360,993 B2
(45) Date of Patent: Jul. 23, 2019

(54) EXTRACT INFORMATION FROM MOLECULAR PATHWAY DIAGRAM

(71) Applicant: International Business Machines Corporation, Armonk, NY (US)

(72) Inventors: Konstantinos Bekas, Horgen (CH); Maria Gabrani, Thalwil (CH); Antonio Foncubierta Rodriguez, Zurich (CH)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/807,874

(22) Filed: Nov. 9, 2017

(65) Prior Publication Data
US 2019/0138686 A1    May 9, 2019

(51) Int. Cl.
*G16B 15/00*     (2019.01)
*G16B 45/00*     (2019.01)
(Continued)

(52) U.S. Cl.
CPC ............ *G16B 15/00* (2019.02); *G06K 9/344* (2013.01); *G06K 9/46* (2013.01); *G06K 9/6256* (2013.01); *G06K 9/726* (2013.01); *G16B 5/00* (2019.02); *G16B 40/00* (2019.02); *G16B 45/00* (2019.02); *G06K 9/469* (2013.01);
(Continued)

(58) Field of Classification Search
CPC .......... G06K 9/469; G06K 9/46; G06K 9/726; G06K 9/344; G06K 9/6256; G06K 2209/01; G06K 2209/27; G16B 15/00; G16B 45/00; G16B 5/00; G16B 40/00; G06N 5/022
See application file for complete search history.

(56) References Cited

U.S. PATENT DOCUMENTS 5,522,022 A * 5/1996 Rao .................... G06K 9/00476
                                                    345/440
9,489,485 B2   11/2016 Koblischke et al.
(Continued)

FOREIGN PATENT DOCUMENTS

WO    2016118513 A1    7/2016

OTHER PUBLICATIONS

Vasudevan et al. "Flowchart Knowledge Extraction on Image Processing." IEEE International Joint Conference on Neural Networks, Jun. 1, 2008, pp. 4075-4082 (Year: 2008).*

(Continued)

*Primary Examiner* — Jon Chang
(74) *Attorney, Agent, or Firm* — Harrington & Smith

(57) ABSTRACT

A method for extracting information from a molecular pathway diagram may be provided. The method includes providing a molecular pathway diagram, detecting basic graphical structural elements in the diagram resulting in a set of basic objects, detecting a graphical semantic of each of the basic graphical structural elements resulting in a set of structural primitives, and detecting a graphical syntax of the basic graphical structural element relative to each other and to the diagram. Furthermore, the method includes assigning metadata to a plurality of the detected basic graphical structural elements, where the metadata includes basic graphical structural element data, graphical semantic data and graphical syntax data resulting in a set of entities and relationships.

20 Claims, 10 Drawing Sheets

(51) Int. Cl.
G16B 5/00 (2019.01)
G16B 40/00 (2019.01)
G06K 9/46 (2006.01)
G06K 9/62 (2006.01)
G06K 9/72 (2006.01)
G06K 9/34 (2006.01)
G06N 5/02 (2006.01)

(52) U.S. Cl.
CPC ..... G06K 2209/01 (2013.01); G06K 2209/27 (2013.01); G06N 5/022 (2013.01)

(56) References Cited

U.S. PATENT DOCUMENTS

| 2004/0090439 | A1* | 5/2004 | Dillner | G06K 9/00402 345/440 |
| 2015/0186427 | A1 | 7/2015 | Logothetis et al. | |
| 2015/0317430 | A1* | 11/2015 | Olson | G06F 19/12 703/11 |
| 2018/0349509 | A1* | 12/2018 | Abou Mahmoud | G06F 17/30958 |

OTHER PUBLICATIONS

G. Feng, C. Viard-Gaudin, and Z. Sun, "On-line hand-drawn electric circuit diagram recognition using 2D dynamic programming," Pattern Recognition, vol. 42, No. 12, pp. 3215-3223, Dec. 2009.
K. D. Forbus, J. Usher, and V. Chapman, "Sketching for Military Courses of Action Diagrams," presented at the Proceedings of the 8th International Conference on Intelligent User Interfaces, Jan. 2003, pp. 61-68.
R. P. Futrelle, I. A. Kakadiaris, J. Alexander, C. M. Carriero, N. Nikolakis, and J. M. Futrelle, "Understanding diagrams in technical documents," Computer, vol. 25, No. 7, pp. 75-78, Jul. 1992.
T. Hammond and R. Davis, "Tahuti: A Geometrical Sketch Recognition System for UML Class Diagrams," presented at the ACM SIGGRAPH 2006 Courses, 2006. [Retrieved Mar. 8, 2018].
J. Mas, G. Sanchez, J. Llados, and B. Lamiroy, "An Incremental On-line Parsing Algorithm for Recognizing Sketching Diagrams," presented at the Ninth International Conference on Document Analysis and Recognition (ICDAR 2007), Sep. 2007.
R. Mörzinger, R. Schuster, A. Horti, and G. Thallinger, "Visual Structure Analysis of Flow Charts in Patent Images.," presented at the CLEF (Online Working Notes/Labs/Workshop), 2012. [Retrieved Mar. 8, 2018].
Y. Nakamura, R. Furukawa, and M. Nagao, "Diagram understanding utilizing natural language text," presented at the Proc. Second Int Document Analysis and Recognition Conf, 1993, pp. 614-618. [Retrieved Mar. 8, 2018].
M. Rusiñol et al., "CVC-UAB's Participation in the Flowchart Recognition Task of CLEF-IP 2012.," presented at the CLEF (Online Working Notes/Labs/Workshop), Jan. 2012.
A. Thean, J.-M. Deltorn, P. Lopez, and L. Romary, "Textual summarisation of flowcharts in patent drawings for CLEF-IP 2012," presented at the CLEF 2012, Sep. 2012.
Y. Watanabe and M. Nagao, "Diagram Understanding Using Integration of Layout Information and Textual Information," presented at the Proceedings of the 17th International Conference on Computational Linguistics—vol. 2, 1998, pp. 1374-1380. [Retrieved Mar. 8, 2018].
W.-T. Zheng and Z.-X. Sun, "Knowledge-based hierarchical sketch understanding," presented at the Proc. Int. Conf. Machine Learning and Cybernetics, Aug. 2005, vol. 5, p. 2838-2843 vol. 5.
G. Butler, P. Grogono, R. Shinghal, and I. Tjandra, "Retrieving information from data flow diagrams," presented at the Proc. 2nd Working Conf. Reverse Engineering, 1995, pp. 22-29. [retrieved Mar. 27, 2018].
E. Lank, J. Thorley, S. Chen, and D. Blostein, "On-line recognition of UML diagrams," presented at the Proceedings of Sixth International Conference on Document Analysis and Recognition, 2001. [retrieved Mar. 27, 2018].

* cited by examiner

EXTRACT INFORMATION FROM MOLECULAR PATHWAY DIAGRAM

FIELD OF THE INVENTION

The invention relates generally to a method for extracting information from a molecular pathway diagram. The invention relates further to a related system for extracting information from a molecular pathway diagram, and a computer program product.

BACKGROUND

Science is a cumulative task, where new knowledge is always built upon prior knowledge. Science production, in the form of conference proceedings, presentations and scientific articles is constantly expanding. A resulting information overload requires updated computer-based tools to make knowledge accessible and, most importantly, searchable and interpretable. The goal of making information accessible and reusable for future research requires understanding not only text but also graphical information.

Specific fields, including personalized medicine, drug discovery, pharmacovigilance (e.g., drug safety) and systems biology make intensive use of graphical information to provide added value to written text in scientific publications. Molecule pathway diagrams are one major way used by scientists aiming at summarizing, describing and representing complex relationships between various biological entities. The term molecular pathway is used in this document as a common denomination of metabolic pathways, signal transduction pathway, regulatory networks or genetic pathway, among others. In general, a molecular pathway diagram is a graphical representation of any actions, changes, relations and interactions between the phenotype of a living organism, genes, RNA, proteins, drugs or other molecules.

Molecular pathway diagrams comprising extremely valuable information for researchers may be integrated into searchable databases. These databases may be built and enhanced with the assistance of experts that manually curate each of the relations that are included in the database, often combining text mining on published sources and additional tools for discovery, conflicting resolutions and integration. However, these tools, and thus the content of the database, typically neglect the information that is contained in the images that accompany the publications.

A series of publications has been made in this field, e.g.:

Document WO 2016118513 A1 discloses a method and associated system for analyzing biological networks. The method includes obtaining data representing biological networks from one or more data stores and obtaining data representing biological pathways, such as pathways defined for the biological networks. The biological networks are defined by respective nodes representing molecules and connections representing relationships between or among the molecules.

Document US 20150186427 A1 discloses a method and a system for analyzing dynamic graphs. It is described that computations are performed at a plurality of graph vertices every time a change in the graph occurs. In order to minimize the computational load of each computational iteration, previous computation results are reused when the inputs for a computation at a given vertex are unchanged from previous computations.

However, typical cognitive computing systems are still sort of blind to graphics and documents including documents comprising molecular or pathway diagrams. Thus, there is a need for a better interpretation, categorization and/or classification of content contained in graphical representations of complex relationships of entities.

SUMMARY

According to an embodiment of the present invention, a method is provided for extracting information from a molecular pathway diagram, the method including: providing a molecular pathway diagram, detecting basic graphical structural elements in the molecular pathway diagram resulting in a set of basic objects, detecting a graphical semantic of each of the basic graphical structural elements resulting in a set of structural primitives, detecting a graphical syntax of the basic graphical structural elements relative to each other and to the molecular pathway diagram, and assigning metadata to a plurality of the detected basic graphical structural elements resulting in a set of entities and relationships, the metadata comprising data corresponding to the basic graphical structural elements, data corresponding to the graphical semantic of each of the basic graphical structural elements and data corresponding to the graphical syntax.

According to an embodiment of the present invention, a system for extracting information from a molecular pathway diagram is provided. The system including: at least one processor; at least one memory including computer program code, the at least one memory and the computer program code configured to, with the at least one processor, cause the system at least to: select a molecular pathway diagram from a storage system, detect basic graphical structural elements in the molecular pathway diagram resulting in a set of basic objects, detect a graphical semantic of each of the basic graphical structural elements resulting in a set of structural primitives, detect a graphical syntax of the basic graphical structural elements relative to each other and to the molecular pathway diagram, and assign metadata to a plurality of the detected basic graphical structural elements resulting in a set of entities and relationships, the metadata comprising data corresponding to the basic graphical structural elements, data corresponding to the graphical semantic of each of the basic graphical structural elements and data corresponding to the graphical syntax.

According to an embodiment of the present invention, a computer program product for extracting information from a molecular pathway diagram is provided. The computer program product includes a computer readable storage medium having program instructions embodied therewith, the program instructions being executable by one or more computing systems to cause the one or more computing systems to: provide a molecular pathway diagram, detect basic graphical structural elements in the molecular pathway diagram resulting in a set of basic objects, detect a graphical semantic of each of the basic graphical structural elements resulting in a set of structural primitives, detect a graphical syntax of the basic graphical structural element relative to each other and to the molecular pathway diagram, and assign metadata to a plurality of the detected basic graphical structural elements resulting in a set of entities and relationships, the metadata comprising data corresponding to the basic graphical structural elements, data corresponding to the graphical semantic of each of the basic graphical structural elements and data corresponding to the graphical syntax.

BRIEF DESCRIPTION OF THE DRAWINGS

It should be noted that embodiments of the invention are described with reference to different subject-matters. In particular, some embodiments are described with reference to method type claims, whereas other embodiments have been described with reference to apparatus type claims. However, a person skilled in the art will gather from the above and the following description that, unless otherwise notified, in addition to any combination of features belonging to one type of subject-matter, also any combination between features relating to different subject-matters, in particular, between features of the method type claims, and features of the apparatus type claims, is considered as to be disclosed within this document.

The aspects defined above, and further aspects of the present invention, are apparent from the examples of embodiments to be described hereinafter and are explained with reference to the examples of embodiments, but to which the invention is not limited.

Figure 1:
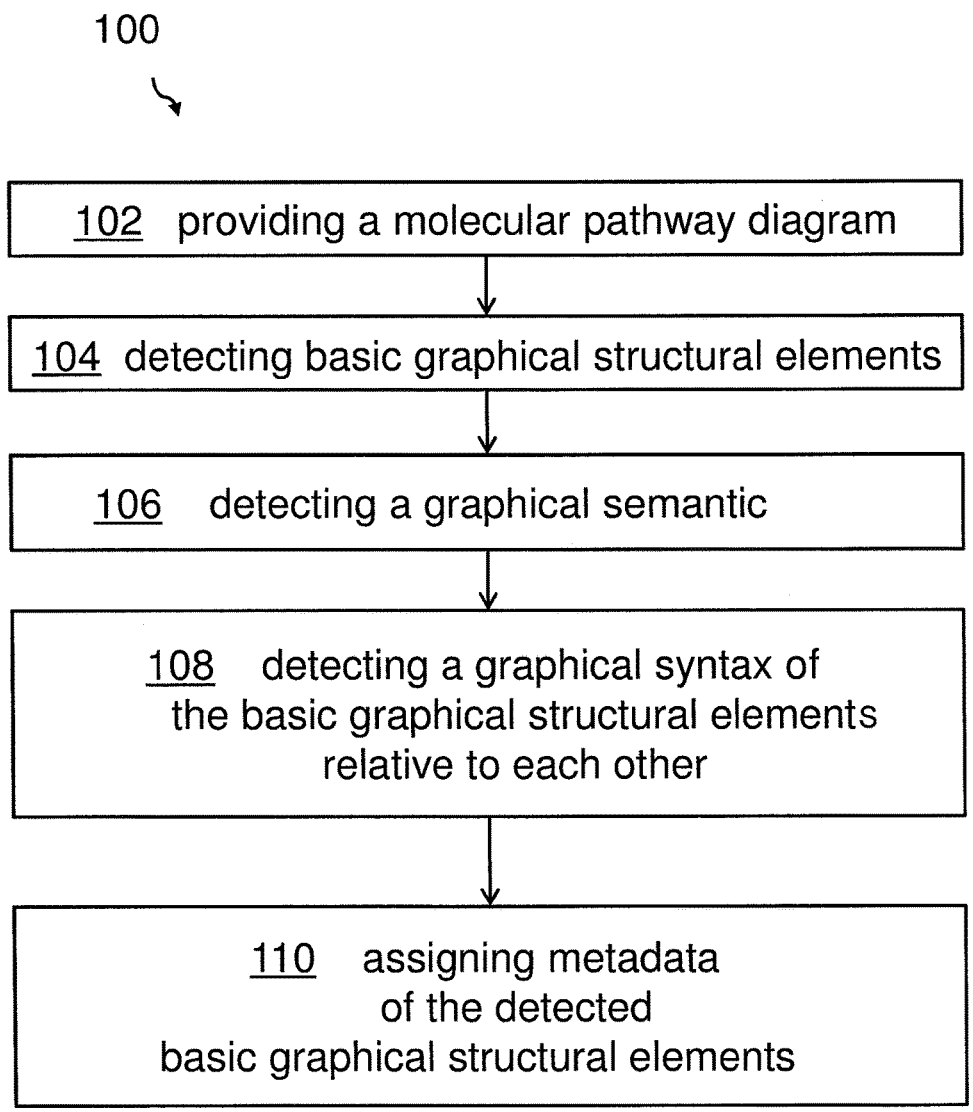

Preferred embodiments of the invention will be described, by way of example only, and with reference to the following drawings:

FIG. 1 shows a block diagram of an embodiment of the inventive method for extracting information from a molecular pathway diagram.

Figure 2:
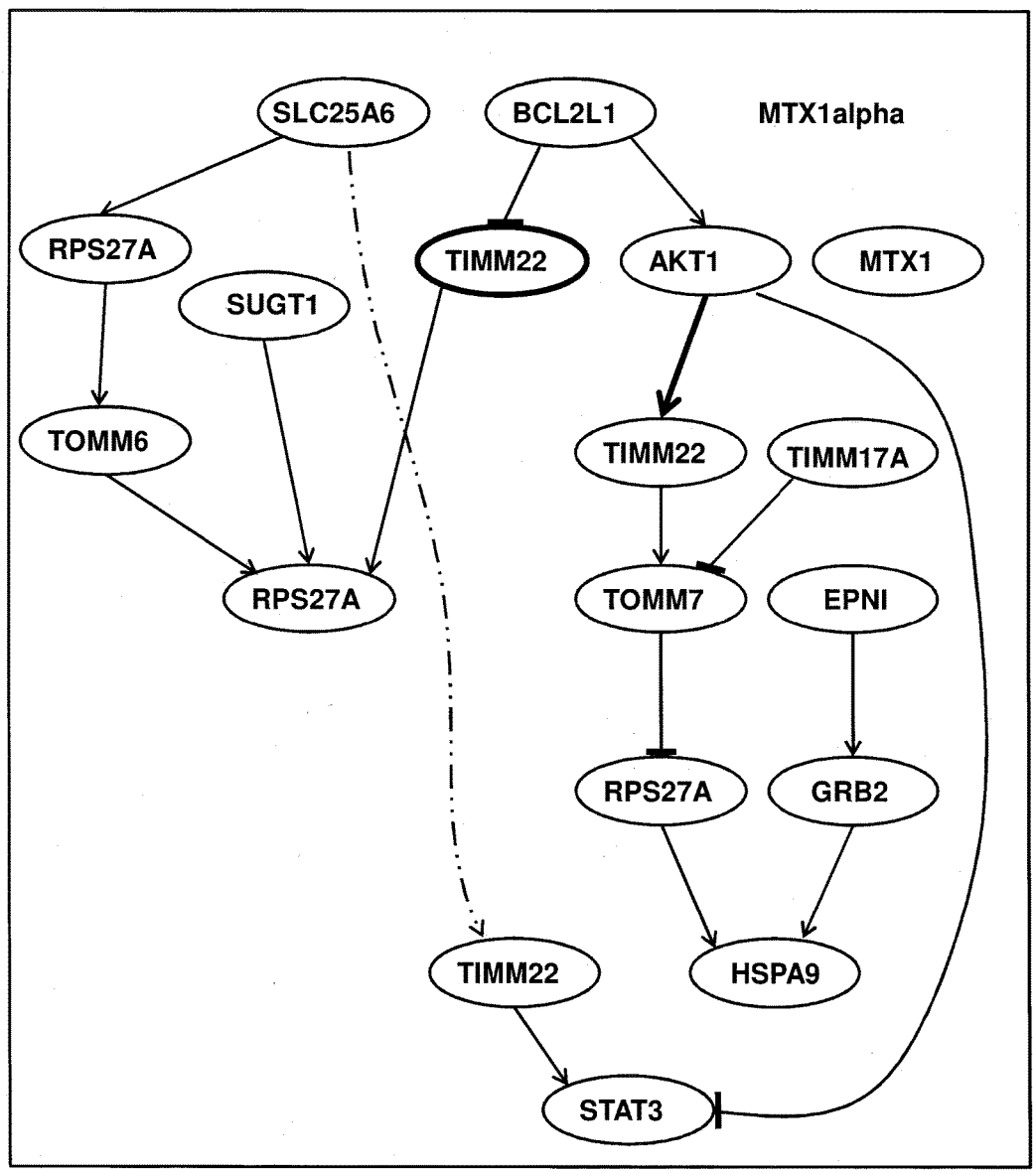

FIG. 2 shows a block diagram of an embodiment of a molecular pathway diagram.

Figure 3:
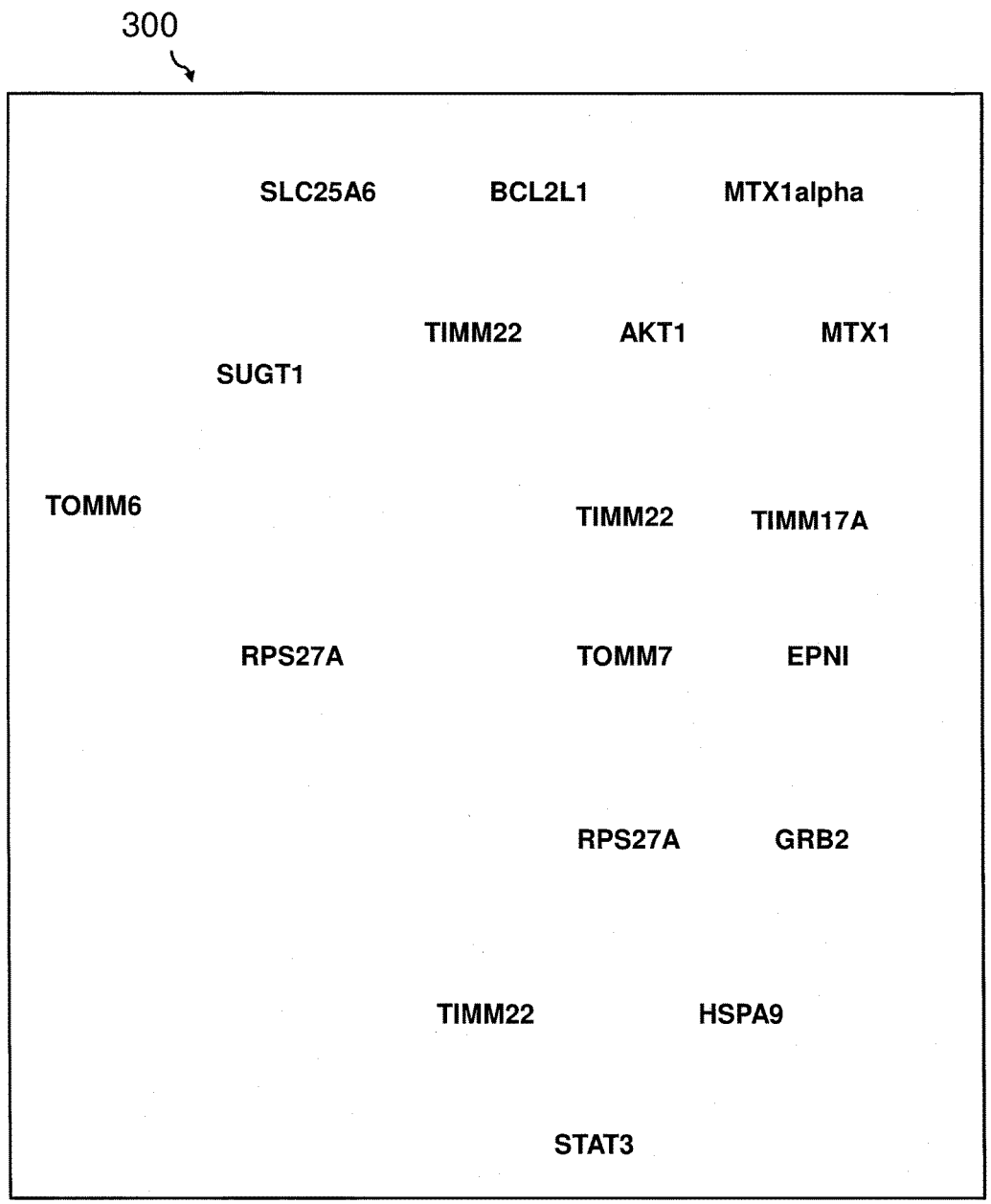

FIG. 3 shows a diagram of detected characters of the molecular pathway diagram of FIG. 2.

Figure 4:
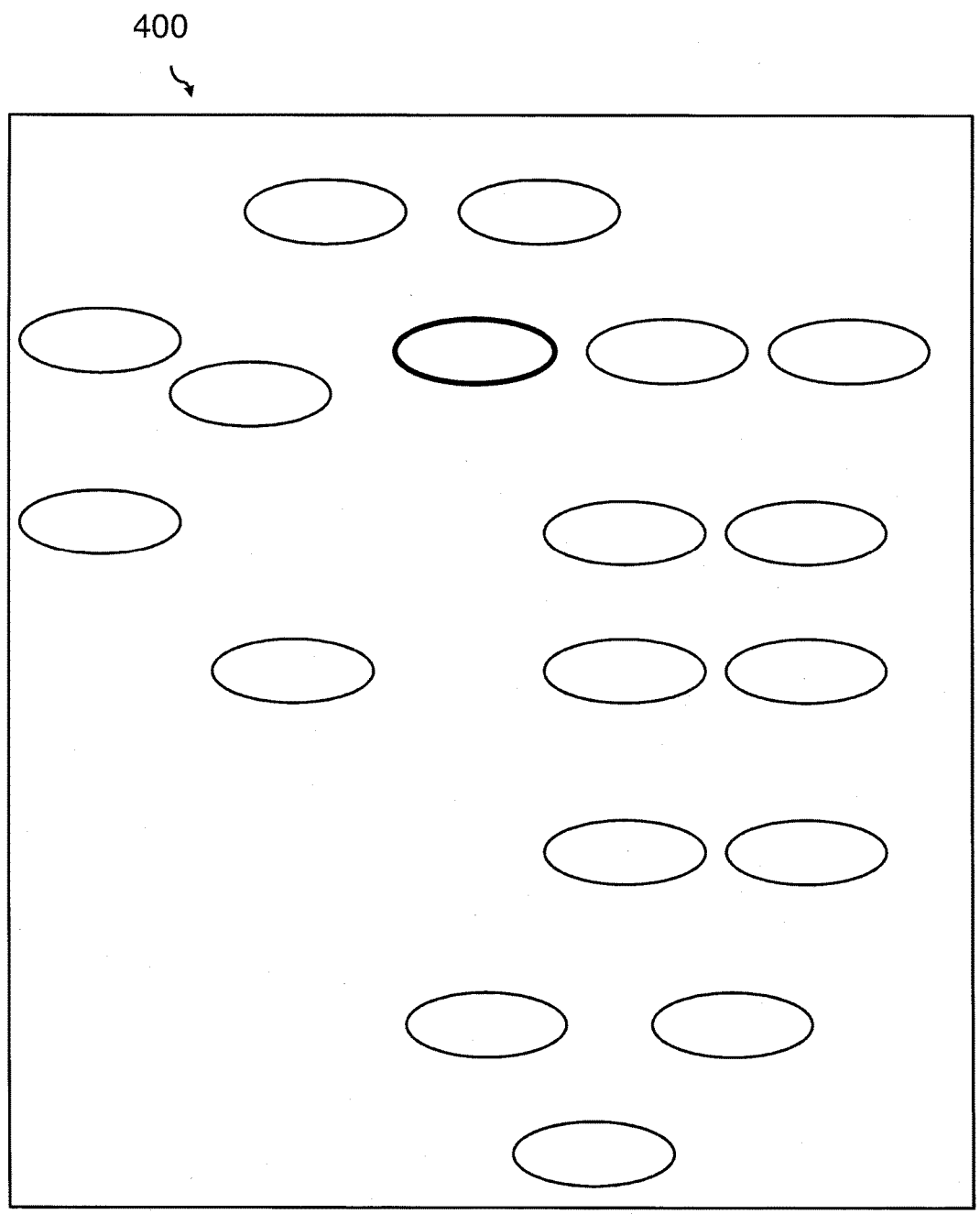

FIG. 4 shows a diagram of detected ellipses as examples for closed shapes in the molecular pathway diagram of FIG. 2.

Figure 5:
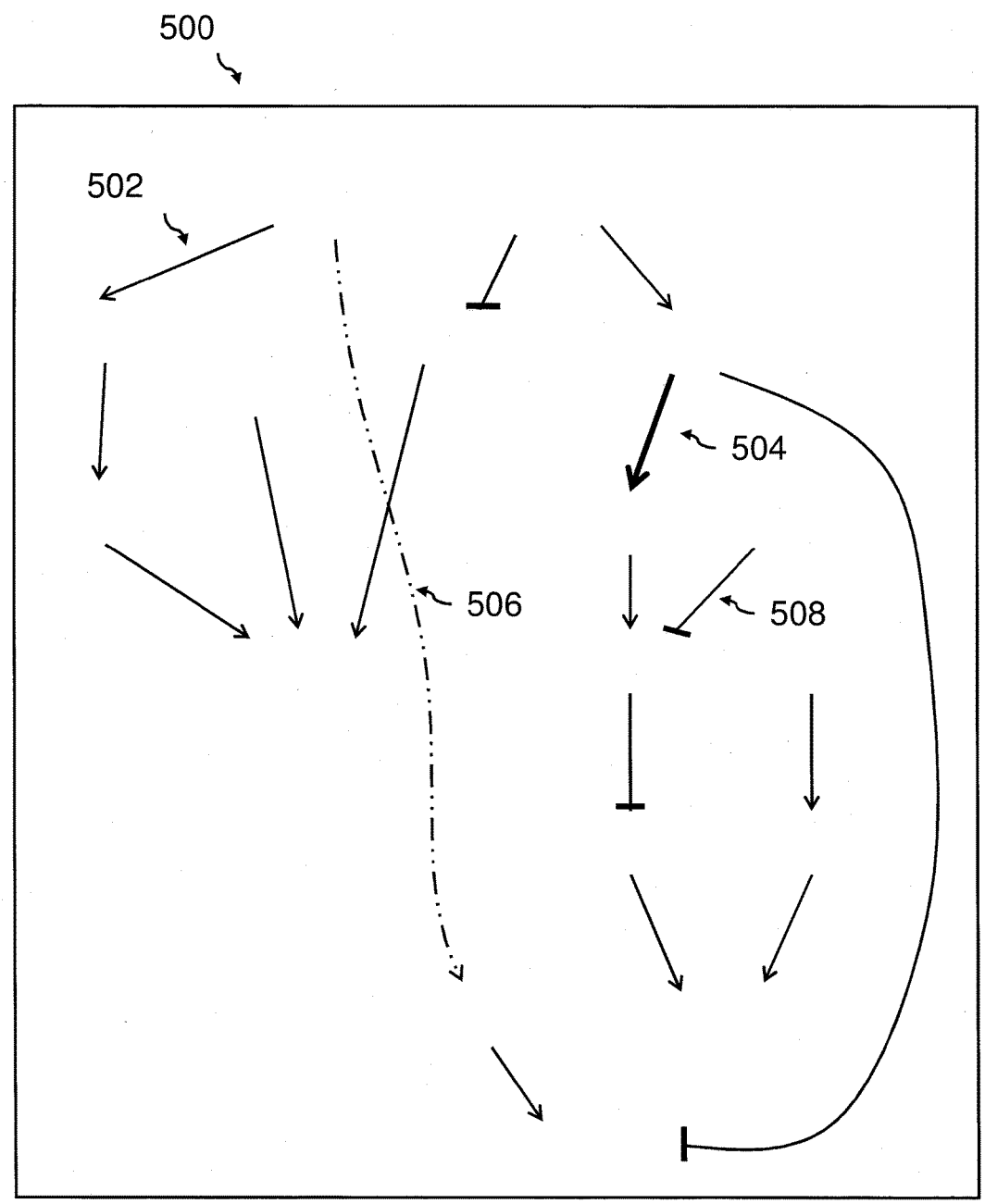

FIG. 5 shows a diagram of detected polylines in the molecular pathway diagram of FIG. 2.

Figure 6:
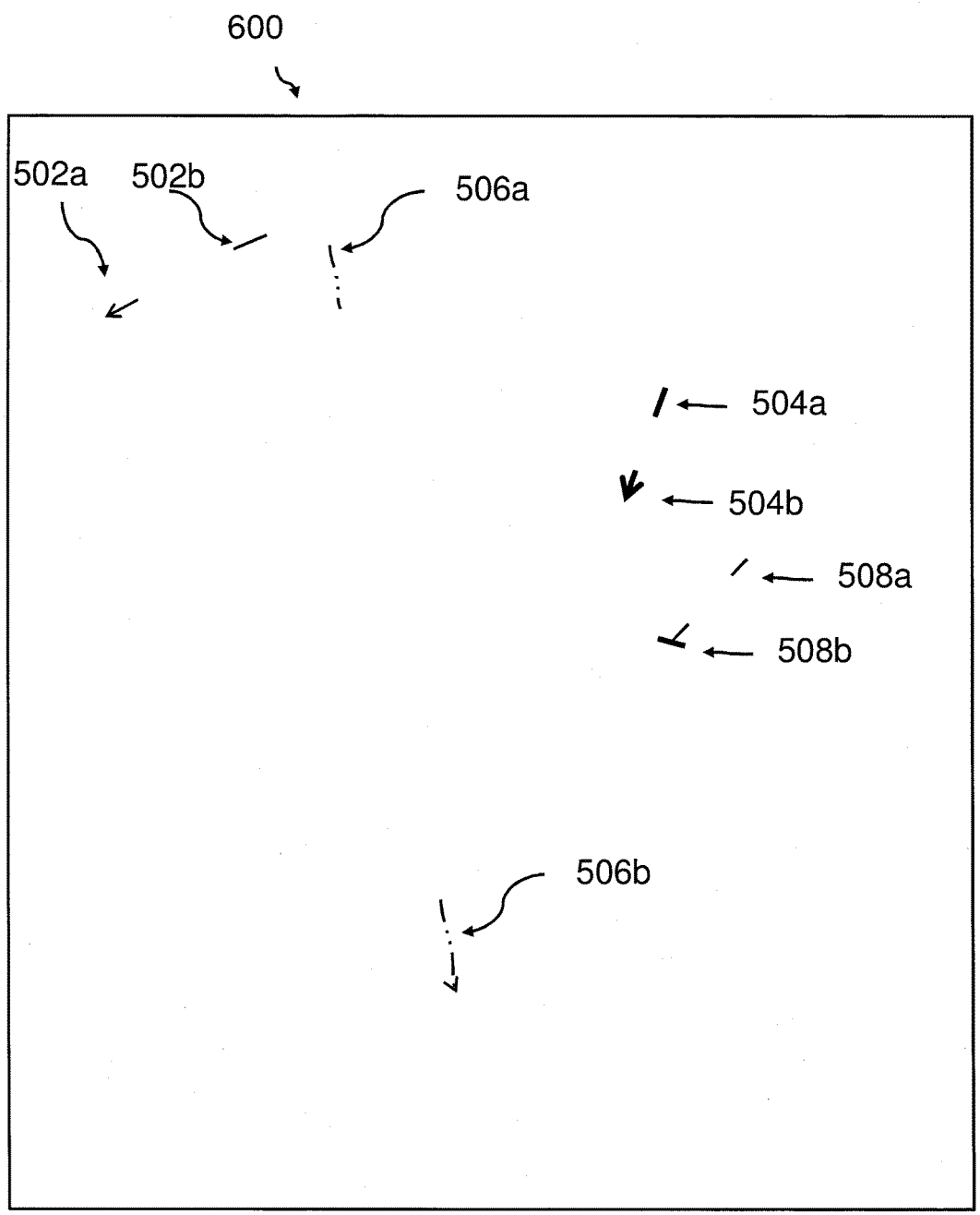

FIG. 6 shows a diagram of detected connection nodes in the molecular pathway diagram of FIG. 2.

Figure 7:
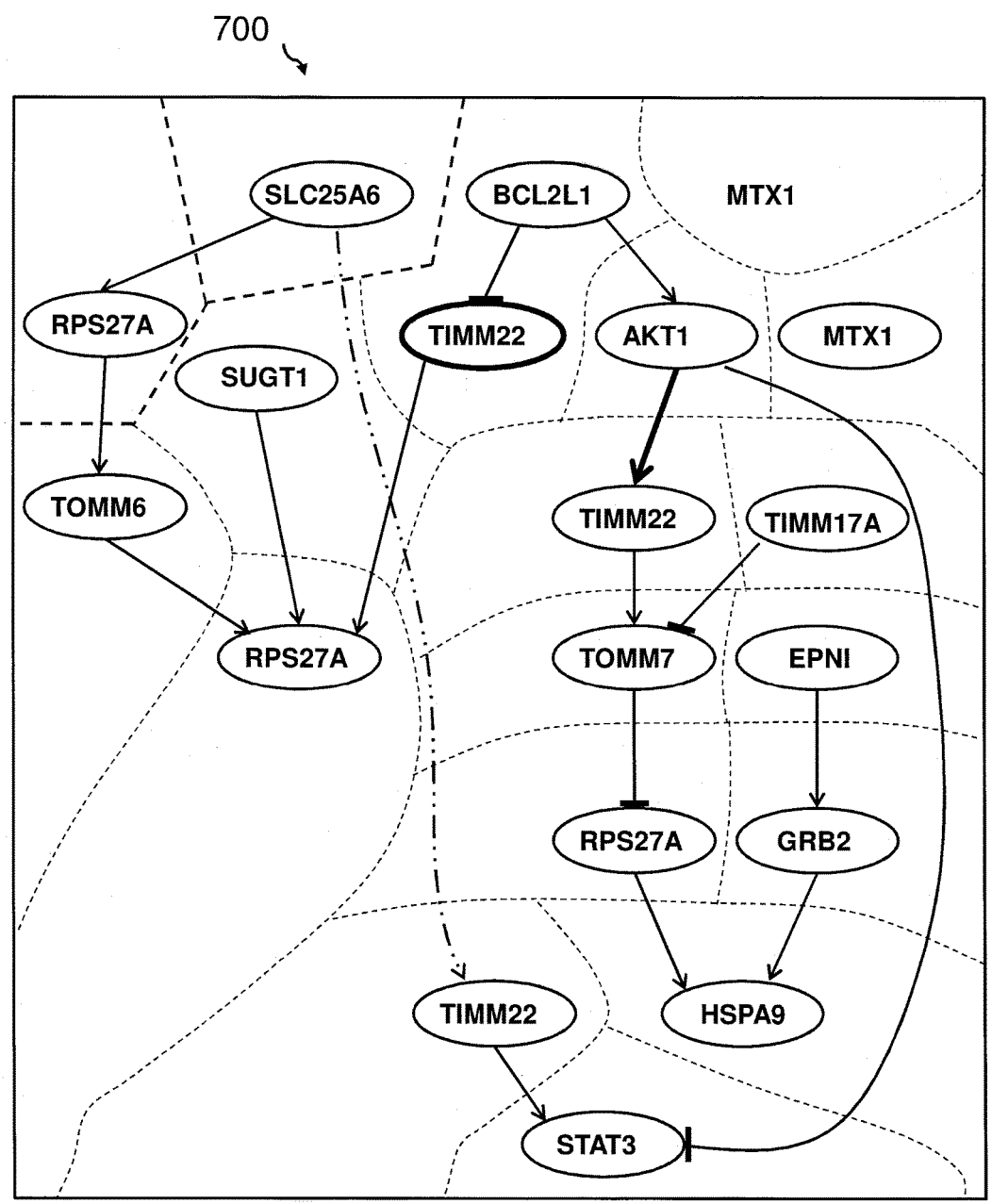

FIG. 7 shows a diagram of detected content nodes via a Voronoi diagram in the molecular pathway diagram of FIG. 2.

Figure 8:
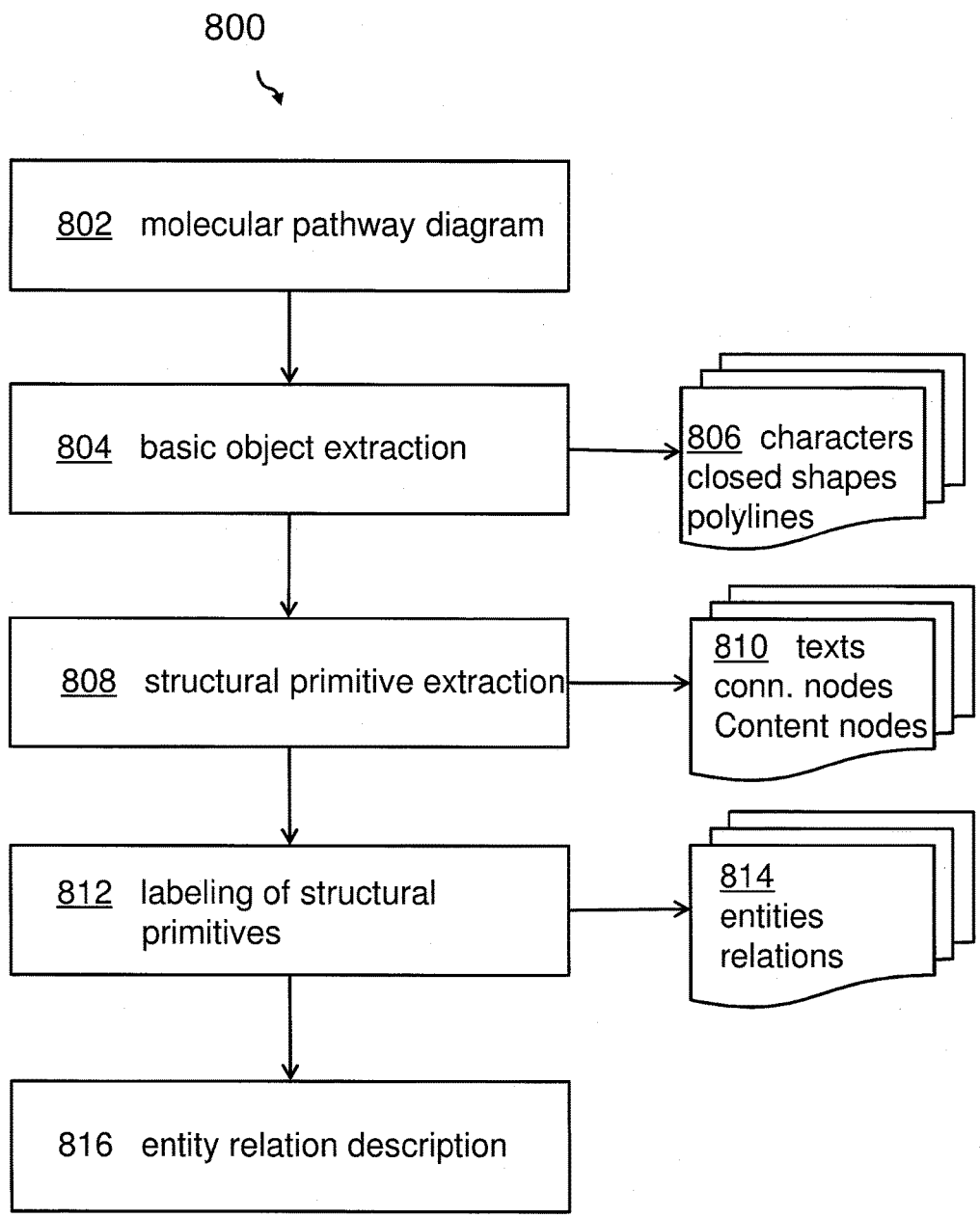

FIG. 8 shows a flowchart of a more technical block diagram of the proposed method.

Figure 9:
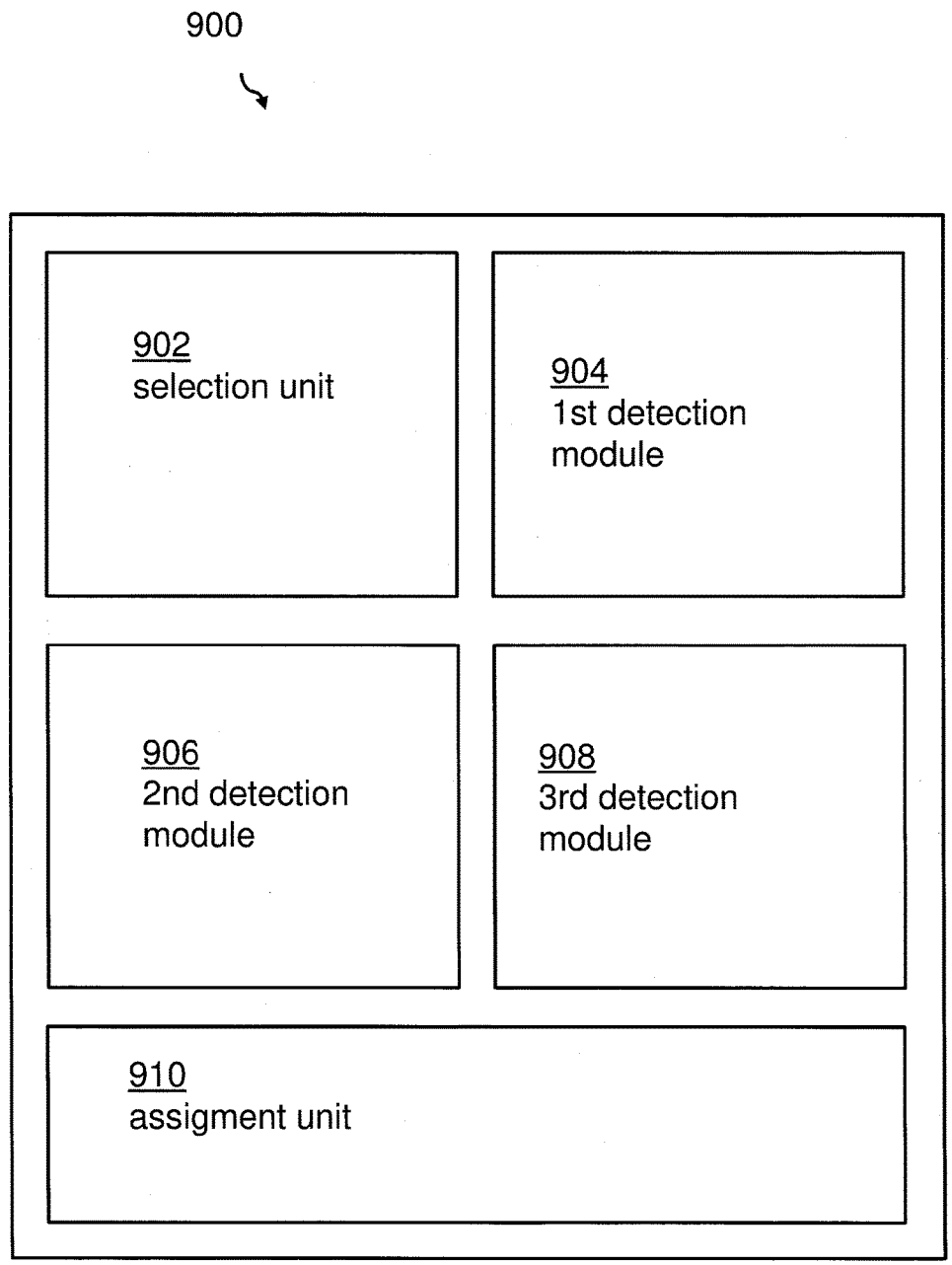

FIG. 9 shows a block diagram of an embodiment of the system for extracting information from a molecular pathway diagram.

Figure 10:
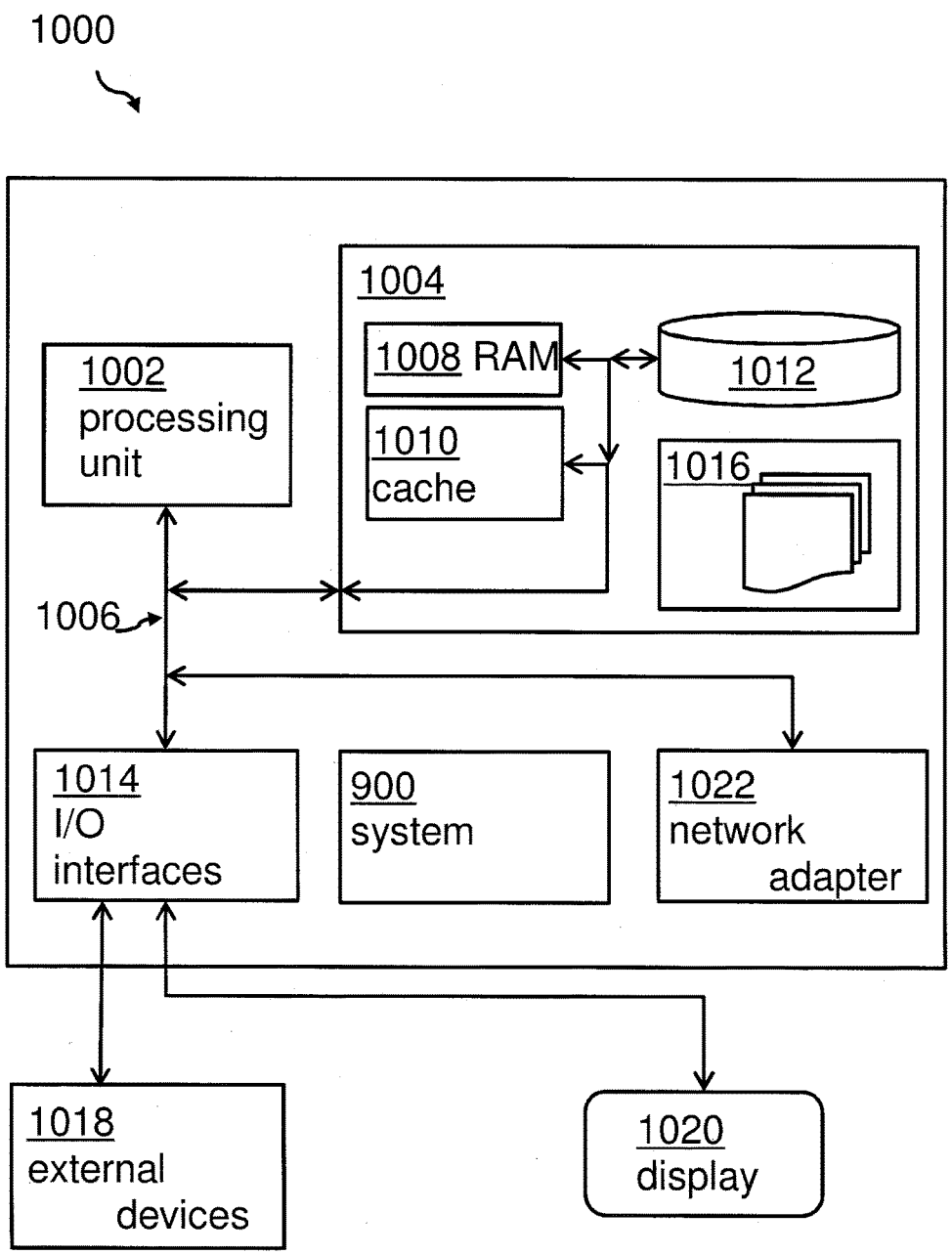

FIG. 10 shows a block diagram of an embodiment of a computing system comprising the system according to FIG. 9.

DETAILED DESCRIPTION

In the context of this description, the following conventions, terms and/or expressions may be used:

The term 'molecular pathway diagram' may denote a directed graph with the content nodes—also known as nodes—and connections—also known as edges between the nodes. These types of diagrams are typically used in a large variety and may be combined with additional drawings, and may have various shapes and information density. They typically describe interaction, changes from one status to another, relationship of entities (e.g., proteins, genes, RNA, . . . ) and so on. They may be found in scientific documents, manually curated databases as well as published diagrams. Their common goal may be in understanding biological, drug discovery and/or personalized medicine. The molecular pathway diagrams may typically be provided in pixel form or in vector graphic form. However, also other graphics formats may be allowed.

The term 'basic graphical structural elements' may denote closed shapes, lines, curves, arrows as well as characters, symbols, letters or numbers of different character sets. These basic graphical structural elements may be the building blocks of for molecular pathway diagrams.

The term 'graphical semantic' may denote a location, a size, a color, and appearance like the shape, transparency, texture, or any other visual feature like border characteristics (color, boldness, double-blind, etc.) and further visual elements of basic graphical structural elements. In the same sense, a related 'graphical syntax' may denote a relative position, inclusion/exclusion, distance, intersection, continuity between two elements (i.e., smoothness of a connection line) of the basic graphical structural elements.

The term 'metadata' may denote data/information that may provide information about other data. Three distinct types of metadata exist: descriptive metadata, structural metadata, and administrative metadata. Descriptive metadata may describe a resource for purposes such as discovery and identification. It may include elements such as title, abstract, author, and keywords, i.e., strings or text elements. Structural metadata may be metadata about containers of data and indicates how compound objects are put together, e.g., how content nodes may be connected to other content nodes. It may describe the types, positions, relationships and other characteristics of digital molecular pathway diagram. Administrative metadata provides information to help manage a resource such as when and how it was created, file type and other technical information, and who can access it. This last type of metadata may typically not be available for the molecular pathway diagrams that should be interpreted.

The term 'connected components' may denote content nodes which may be connected via a polyline. A polyline may have a beginning and an end—often indicated by an arrow on another type of ending, like a short vertical line compared to the polyline—of a line between two content nodes.

The term 'optical character recognition' (OCR) may denote the technology to identify individual characters from pixel information. Although the character recognition may not be done in an optical way because the information is already available in a digital format (i.e., pixels), the name is still used for the known technology.

The term 'confidence correction' may denote a correction of a recognized character by means of OCR in the context of a language model or a dictionary if seen as one element of a string of characters. As an example, "I" may be interpreted as a capital "i" or as a small "L". The context of the string together with the dictionary and/or language model may give the recognized "I" the more probable meaning. This more probable meaning has been used as the confidence corrected character.

The term 'text string' may denote a sequence of individual characters not separated by a larger space in between, i.e., a blank.

The term 'connection node' may denote, e.g., a link between a polyline and the closed shape of a content node. However a connection node may also be a crossing of two polylines. For a correct interpretation of the type of connection node, a graphical context—in particular whether the connection node is a link between a content node and a polyline or a link between two polylines or an overlap of two content nodes—is instrumental in finding them of the identified connection node.

The term 'content node' may denote a closed shape comprising a recognized character or string inside the closed shape. As also mentioned, a closed shape may be a circle, an ellipse, a square, a rectangle, a parallelogram or any other type of polyline encircling in area of the diagram.

The term 'modified Voronoi diagram' may denote a way to partition a given diagram like a molecular pathway diagram. In mathematics, a Voronoi diagram is a partitioning of a plane into regions based on distance to points in a specific subset of the plane. That set of points (called seeds, sites, or generators) is specified beforehand (here, the closed shapes), and for each seed there is a corresponding region consisting of all points closer to that seed than to any other. These regions are called Voronoi cells. In the context of this application, the here used form of the modified Voronoi diagram may be instrumental in isolating content nodes of the molecular pathway diagram.

The term 'cognitive computing model' may denote a technology platform that, broadly speaking, is based on the scientific disciplines of artificial intelligence and signal processing. These platforms encompass machine learning, reasoning, natural language processing, speech recognition and vision (object recognition), human-computer interaction, dialog and narrative generation, among other technologies. In the context of this application, the cognitive computing model may comprise at least one of a rule, a decision making method and/or a reasoning method. In the context of the current description, it may comprise a large plurality of rules, roll models decision-making criteria, application of thresholds and feedback loops.

According to one aspect of the present invention, a method for extracting information from a molecular pathway diagram may be provided. The method may comprise providing a molecular pathway diagram, detecting basic graphical structural elements in the molecular pathway diagram resulting in a set of basic objects, detecting a graphical semantic of each of the basic graphical, structural elements resulting in a set of structural primitives, and detecting a graphical syntax of the basic graphical structural element relative to each other and to the molecular pathway diagram. Furthermore the method may comprise assigning metadata to a plurality of the detected basic graphical structural elements, the metadata comprising basic graphical structural element data, graphical semantic data and graphical syntax data resulting in a set of entities and relationships.

According to another aspect of the present invention, a system for extracting information from a molecular pathway diagram may be provided. The system may comprise a selection unit adapted for selecting a molecular pathway diagram from a storage system, a first detection module adapted for detecting basic graphical structural elements in the molecular pathway diagram resulting in a set of basic objects, a second detection module adapted for detecting a graphical semantic of each of the basic graphical structural elements resulting in a set of structural primitives, and a third detection module adapted for detecting a graphical syntax of the basic graphical structural element relative to each other and to the molecular pathway diagram. Additionally, the system may comprise an assignment unit adapted for assigning metadata to a plurality of the detected basic graphical structural elements, the metadata comprising basic graphical structural element data, graphical semantic data and graphical syntax data resulting in a set of entities and relationships.

Furthermore, embodiments may take the form of a related computer program product, accessible from a computer-usable or computer-readable medium providing program code for use, by or in connection with a computer or any instruction execution system. For the purpose of this description, a computer-usable or computer-readable medium may be any apparatus that may contain means for storing, communicating, propagating or transporting the program for use, by or in a connection with the instruction execution system, apparatus, or device.

The proposed method for extracting information from a molecular pathway diagram may offer multiple advantages and technical effects:

In general, content comprised in structure diagrams, like flowcharts and/or molecular pathways becoming automatically interpretable, categorize and/or classifiable without any human or expert intervention. For that, recognized graphical representations of, e.g., molecular pathways, are divided into basic building blocks and metadata of these building blocks are extracted from the graphical representation. The metadata may comprise all those characteristic elements also interpreted by experts as a way to add context to the basic building blocks. This may comprise text related to a basic building block, color information, font information, line information, encirclement and so on.

Furthermore, the proposed method may also be instrumental interpreting and analyzing graphical semantics and syntax of the basic building blocks. For this, the beforehand extracted metadata of the basic building blocks are used, as well as relative positions of the building blocks and elements relating to a plurality of basic building blocks as isolated from the graphical representation. This process may be supported by a cognitive computing model including a set of machine learning algorithms, rules and decision-making and reasoning algorithms.

Main differences to prior art approaches comprise an abstraction of the low level representation and a conversion into basic graphical elements, i.e., basic objects and structural primitives. There may be no need to train specific shapes to an algorithm because all closed shapes may be detected as graphical elements and described with semantics and syntax for a clear differentiation. Also curves and intersections are fully supported through the representation. There is also no need for the cognitive computing model used to be dependent on concepts like flow direction, sink and source elements.

Thus, the proposed method and related system allows for a robust representation of the graphical representation using a cognitive computing model with extreme variety ability in categories. The proposed method may be used for knowledge data and for inter-document relationship discovery. As structured information is becoming the norm—also from sources like graphical representations—the interpretability, categorization and classification of graphical representations of complex relationships may be enhanced significantly.

Since molecular pathways often refer to known molecules in health sciences, the proposed method may also allow an integration of information from several sources, since the relationships discovered in one diagram can potentially be extended with the ones discovered in other diagrams, enabling the building of a more extensive structured knowledge.

It may also allow reasoning on the relationships at various granularity levels. Being able to extract information about how an entity A interacts with B and B with C may directly map to an understanding of the relation between A and C through B.

It may also allow identifying equivalences between two molecules if they have the same relationships, or even compare the structure of two molecular pathways regardless of what is their pixel-based representation.

Another advantage is that the proposed method allows for discovering interactions that have not been reported in the text of some documents. Due to the limitations of space, not all found interactions can be accurately and extensively described in a text format whereas in a graphical way it is trivial to add one more lines to represent this information. These findings, which were completely neglected until now, are now fully accessible by analyzing diagrams with the proposed method.

In the following, additional embodiments of the inventive concept will be described. Generally, the embodiments may be interpretable in the context of the method, as well as the related system and/or computer program product.

According to one permissive embodiment of the method, the basic graphical structural elements may comprise at least one selected out of the group comprising a closed shape—in particular a circle, an ellipse, a closed polygon like a triangle, a square, a hexagon, etc.—a line, a curve, an arrow and a character. The known principles of the graph theory may be used to identify and correlate the graphical structural elements. Graph theory is known from mathematics as the study of graphs, which are mathematical structures used to model pairwise relations between objects. A graph in this context may be made up of vertices, nodes or points which may be connected by edges, arcs or lines. A graph may be undirected, meaning that there is no distinction between the two vertices associated with each edge or its edges may be directed from one vertex to another.

According to another permissive embodiment of the method, the graphical syntax may comprise at least data selected out of the group comprising a location, a size, a color and an appearance. The appearance may comprise a shape, a transparency, a texture, a border, and/or any other graphical differentiable specialty of a node or an edge. The location information may comprise a location relative to reference point, which may, e.g., be the lower left corner of the related diagram or any other reference point of the related diagram. This way, a relative positioning of any object in the diagram may be defined.

According to one advantageous embodiment of the method, the detection of the graphical syntax may comprise at least one selected out of the group comprising a relative position of the basic graphical structural elements to each other—e.g., by using a geometrical center of each basic graphical structure element—a distance between a pair of relative positions, an inclusion of one of the basic graphical structural elements in another one of the basic graphical structural elements, an intersection—in particular an overlap of one of the basic graphical structural elements with another one of the basic graphical structural elements—and a continuity—in particular smoothness of one of the basic graphical structural elements.

According to one preferred embodiment of the method, a graphical object smaller than a molecular pathway diagram driven threshold value may be interpreted as a character, letter, symbol or number. The threshold value may be dependent on the shape and size of the complete diagrams. Thus, a self-tuning environment adaptable to each form of molecular pathway diagram may be created.

According to another advantageous embodiment, the method may also comprise applying an optical character recognition (OCR) method to sets of detected characters, determining the value of the detected characters—which could be a letter, a number or other symbol relating to a known character set—and applying a confidence correction to a set—in particular a string without a blank—of the detected characters, e.g., by using dictionaries and language models to correct the OCR detected string. It may also be useful to apply probability value assignments. It may be noted that the OCR may not use an optical recognition directly (because the data are already available in binary form after the scanning and not only in optical form), but the same technology used for the character recognition that is used in OCR.

According to another preferred embodiment of the method, the set of structural primitives may comprise a text string, a connection node and/or a content node. Thus, also basic elements with a special meaning in the context of molecular pathway diagrams may be isolated.

According to one optional embodiment, the method may also comprise applying a modified Voronoi diagram method using the closed shapes—in particular those isolated and detected before—as starting point. It may be noted that in standard Voronoi diagrams all areas should be convex; in the modified Voronoi diagram also concave areas are allowable. This option may add another analysis element to the already applied analysis options discussed before.

According to a further advantageous embodiment, the method may also comprise applying a cognitive computing model to the entities and relations. Thus, a trainable machine learning and/or deep learning system may be used to interpret the basic structural elements either to speed up the recognition process or to support in situations the classical analysis approach may fail or may be imprecise.

According to one additionally advantageous embodiment of the method, the application of the cognitive computing model comprises at least one selected out of the group comprising a rule, a decision making method (e.g., decision tree) and/or a reasoning method. This may be based on probabilistic graphical models, e.g., MLN (Markow Logic Network), MRF (Markow Random Field), BN (Bayesian Network), or other machine learning, artificial or augmented intelligence techniques. Thus, the full spectrum of available interpretation methods for graphical relationships may be implemented as part of the method.

It may also be noted that the rules may comprise determination rules point about facts that entities may have a shape that has a specific form or an appearance (e.g., font, color, size) may suggest a specific meaning of the content. The determination rules may also comprise typical forms of connection notes like endpoints of the sections and/or that relations (relationship lines) go typically from one endpoint to another endpoint directly. Another typical rule may comprise determination rules about the fact that relations may few direct changes than others and/or that a start of a relation/connection is the endpoint of the connection with fewer foreground pixels (i.e., not the arrow-portion of the connection line) than the other end of the connection line (i.e., comprising the arrow part).

Furthermore, embodiments may take the form of a related computer program product, accessible from a computer-usable or computer-readable medium providing program code for use, by or in connection with a computer or any instruction execution system. For the purpose of this description, a computer-usable or computer-readable medium may be any apparatus that may contain means for storing, communicating, propagating or transporting the program for use, by or in a connection with the instruction execution system, apparatus, or device.

In the following, a detailed description of the figures will be given. All instructions in the figures are schematic. Firstly, a block diagram of an embodiment of the inventive method for extracting information from a molecular pathway diagram is given. Afterwards, further embodiments, as well as embodiments of the system for extracting information from a molecular pathway diagram, will be described.

FIG. 1 shows a block diagram of an embodiment of the method 100 for extracting information from a molecular pathway diagram. The method 100 comprises providing, 102, a molecular pathway diagram. The molecular pathway diagram may be retrieved from a storage and may be stored in pixel form. The method 100 comprises further detecting, 104, basic graphical structural elements (detailed below) in the molecular pathway diagram resulting in a set of basic objects like characters, closed shapes and polylines, etc.

Additionally, the method 100 comprises detecting, 106, a graphical semantic of each of the basic graphical structural elements resulting in a set of structural primitives—details see below—and detecting, 108, a graphical syntax of the basic graphical structural elements relative to each other and to the molecular pathway diagram as a whole, and assigning metadata, 110, in particular those describing what has been found during the detection phases, e.g., in alpha-numerical form to a plurality—in particular to all, but potentially only to a subset—of the detected basic graphical structural elements. It may be noted that the metadata comprise basic graphical structural element data, graphical semantic data and graphical syntax data resulting in a set of entities and relationships, i.e., nodes and edges of the related graph.

FIG. 2 shows a block diagram 200 of an embodiment of a molecular pathway diagram. As can be seen, it has a form of a directed graph with typed entities, traditionally used for proteins, genes, phenotype description and so on. The typical relations comprise typically activations, invitations, degradations and so on. All of those are recognizable and interpretable by the proposed technology. It may also be noted that some of the shown elements are marked bold (e.g., TIMM22); in other cases an arrow is marked bold, whereas another connection line is marked in dotted lines. Furthermore, there is also descriptive text outside of any encircled graphical element. It may also be noted that the ellipses are only examples of any kind of closed line like circles, squares, polylines, etc.

FIG. 3 shows a diagram 300 of detected characters of the molecular pathway diagram of FIG. 2. It may represent a first step of the basic object detection. Objects smaller than a data-driven threshold—in particular, defined by the total size of the molecular pathway diagram size, e.g., measured in pixels—are interpreted as characters or other symbols, as mentioned. Thus, all other graphical elements of the molecular pathway are eliminated.

FIG. 4 shows a diagram 400 of detected ellipses as examples for closed shapes in the molecular pathway diagram of FIG. 2. This may represent the next step of the basic object detection: closed shapes—in particular lines surrounding a defined area—are extracted including additional metadata about the closed shapes like color, line thickness, position (it may be useful to use the same reference point for each closed shape, e.g., a geometrical center or a lower left corner, etc.) as well as area attributes of the closed shape.

FIG. 5 shows a diagram 500 of detected polylines in the molecular pathway diagram of FIG. 2. In this step of the basic object detection, remaining components are interpreted as polylines. It may be noted that exemplary ones of the polylines are marked with reference numerals (502, . . . , 508). These will be used for the description of FIG. 6.

FIG. 6 shows a diagram 600 of detected connections in the molecular pathway diagram of FIG. 2. This step is a portion of the analysis of structural primitives. This analysis step focuses on singular small portions of the polylines, in particular on the beginning and the end in order to capture direction of polylines, e.g., a starting point and an end point of an arrow. The mathematical smoothness is used as an interpretation aid for capturing the correct meaning of dashed lines.

Hence, for the sake of the example, the elements 502, 504, 506 and 508 of FIG. 5 are analyzed in more depth in the analysis step illustrated by FIG. 6. In a real application, all basic graphical elements are analyzed in comparable detail. Thus, the system develops a clear relationship between beginnings and ends of the elements, in particular 502$a$ and 502$b$, 504$a$ and 504$b$, 506$a$ and 506$b$, as well as 508$a$ and 508$b$.

FIG. 7 shows a diagram 700 of detected content nodes via a Voronoi diagram in the molecular pathway diagram of FIG. 2. In this step, the content nodes are analyzed. For this, the plane of the molecular pathway diagram is partitioned into regions based on distance of two points in a specific subset of the plane. These are then—in the meaning of the Voronoi diagram theory—treated as seeds, sites on generators, and in this case, as the content nodes—put in context of the characters which have been interpreted as strings of characters using OCR-like technology in order to interpret the different signs. It may be noted that this step belongs to the interpretation of the structural primitives which may be performed after the basic object detection. After the OCR-like recognition also a probability value may be determined based on a confidence level of the OCR-like recognition. The recognized characters/string may be aligned with a language model, dictionaries and so on.

E.g., the geometric center of the closed shape may be used as a seed ensuring also that no partition border is crossing a closed shape. Alternatively, the modified Voronoi diagram distance measurement may be based on the border of the closed shape.

FIG. 8 shows a flowchart 800 of a more technical block diagram of the proposed method. Here, the different steps of the method are explained more comprehensively. Firstly, the molecular pathway diagram may be provided, 802, e.g., from a storage system. In the next step, the basic object extraction is performed, 804. As a result 806 characters, closed shapes and polylines are extracted, as explained above. Then, structural primitive elements are extracted, 808. The result 810 can be summarized as interpreted texts, connections between nodes, content nodes, and potentially additional descriptive texts. Some of these texts/strings may be related to individual connections depending on a shortest distance between the text outside a closed shape and a connection line.

In the next step, a labeling of the structural primitives is performed, 812. Using the information of the steps before, the collected information represents individual entities as well as relations (814) which may together be expressed as an entity-relationship description. This forms the extracted information of the molecular pathway diagram and may be stored in a structured database, 816.

FIG. 9 shows a block diagram of an embodiment of the system 900 for extracting information from a molecular pathway diagram. The system 900 comprises a selection unit 902 adapted for selecting a molecular pathway diagram from a storage system (not shown), a first detection module 904 adapted for detecting basic graphical structural elements in the molecular pathway diagram resulting in a set of basic objects, a second detection module 906 adapted for detecting a graphical semantic of each of the basic graphical structural elements resulting in a set of structural primitives, and a third detection module 908 adapted for detecting a graphical syntax of the basic graphical structural element relative to each other and to the molecular pathway diagram.

Last but not least, the system 900 also comprises an assignment unit 910 adapted for assigning metadata to a plurality of the detected basic graphical structural elements, the metadata comprising basic graphical structural element data, graphical semantic data and graphical syntax data resulting in a set of entities and relationships. The last mentioned unit basically performs the last step 816 of FIG. 8, namely making the elements of the molecular pathway diagram machine readable in a structured way in which the information is stored in a structured database.

Embodiments of the invention may be implemented together with virtually any type of computer, regardless of the platform being suitable for storing and/or executing program code. FIG. 10 shows, as an example, a computing system 1000 suitable for executing program code related to the proposed method.

The computing system 1000 is only one example of a suitable computer system and is not intended to suggest any limitation as to the scope of use or functionality of embodiments of the invention described herein. Regardless, computer system 1000 is capable of being implemented and/or performing any of the functionality set forth hereinabove. In the computer system 1000, there are components, which are operational with numerous other general purpose or special purpose computing system environments or configurations. Examples of well-known computing systems, environments, and/or configurations that may be suitable for use with computer system/server 1000 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like. Computer system/server 1000 may be described in the general context of computer system-executable instructions, such as program modules, being executed by a computer system 1000. Generally, program modules may include routines, programs, objects, components, logic, data structures, and so on that perform particular tasks or implement particular abstract data types. Computer system/server 1000 may be practiced in distributed cloud computing environments where tasks are performed by remote processing devices that are linked through a communications network. In a distributed cloud computing environment, program modules may be located in both local and remote computer system storage media including memory storage devices.

As shown in the figure, computer system/server 1000 is shown in the form of a general-purpose computing device. The components of computer system/server 1000 may include, but are not limited to, one or more processors or processing units 1002, a system memory 1004, and a bus 1006 that couples various system components including system memory 1004 to the processor 1002. Bus 1006 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus. Computer system/server 1000 typically includes a variety of computer system readable media. Such media may be any available media that is accessible by computer system/server 1000, and it includes both, volatile and non-volatile media, removable and non-removable media.

The system memory 1004 may include computer system readable media in the form of volatile memory, such as random access memory (RAM) 1008 and/or cache memory 1010. Computer system/server 1000 may further include other removable/non-removable, volatile/non-volatile computer system storage media. By way of example only, storage system 1012 may be provided for reading from and writing to a non-removable, non-volatile magnetic media (not shown and typically called a 'hard drive'). Although not shown, a magnetic disk drive for reading from and writing to a removable, non-volatile magnetic disk (e.g., a 'floppy disk'), and an optical disk drive for reading from or writing to a removable, non-volatile optical disk such as a CD-ROM, DVD-ROM or other optical media may be provided. In such instances, each can be connected to bus 1006 by one or more data media interfaces. As will be further depicted and described below, memory 1004 may include at least one program product having a set (e.g., at least one) of program modules that are configured to carry out the functions of embodiments of the invention.

The program/utility, having a set (at least one) of program modules 1016, may be stored in memory 1004 by way of example, and not limitation, as well as an operating system, one or more application programs, other program modules, and program data. Each of the operating system, one or more application programs, other program modules, and program data or some combination thereof, may include an implementation of a networking environment. Program modules 1016 generally carry out the functions and/or methodologies of embodiments of the invention as described herein.

The computer system/server 1000 may also communicate with one or more external devices 1018 such as a keyboard, a pointing device, a display 1020, etc.; one or more devices that enable a user to interact with computer system/server 1000; and/or any devices (e.g., network card, modem, etc.) that enable computer system/server 1000 to communicate with one or more other computing devices. Such communication can occur via Input/Output (I/O) interfaces 1014. Still yet, computer system/server 1000 may communicate with one or more networks such as a local area network (LAN), a general wide area network (WAN), and/or a public network (e.g., the Internet) via network adapter 1022. As depicted, network adapter 1022 may communicate with the other components of computer system/server 1000 via bus 1006. It should be understood that although not shown, other hardware and/or software components could be used in conjunction with computer system/server 1000. Examples, include, but are not limited to: microcode, device drivers, redundant processing units, external disk drive arrays, RAID systems, tape drives, and data archival storage systems, etc.

Additionally, the system for extracting information from a molecular pathway diagram 900 may be attached to the bus system 1006. In some embodiments, the modules 904, 906, 908 and units 902, 910 may be implemented as one or more components of computer system/server 1000, such as processing unit 1002 and/or memory 1004 for example.

The descriptions of the various embodiments of the present invention have been presented for purposes of illustration, but are not intended to be exhaustive or limited to the embodiments disclosed. Many modifications and variations will be apparent to those of ordinary skills in the art without departing from the scope and spirit of the described embodiments. The terminology used herein was chosen to best explain the principles of the embodiments, the practical application or technical improvement over technologies found in the marketplace, or to enable others of ordinary skills in the art to understand the embodiments disclosed herein.

The present invention may be embodied as a system, a method, and/or a computer program product. The computer program product may include a computer readable storage medium (or media) having computer readable program instructions thereon for causing a processor to carry out aspects of the present invention.

The medium may be an electronic, magnetic, optical, electromagnetic, infrared or a semi-conductor system for a propagation medium. Examples of a computer-readable medium may include a semi-conductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), DVD and Blu-Ray-Disk.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object-oriented programming language such as Smalltalk, C++ or the like, and conventional procedural programming languages, such as the "C" programming language or similar programming languages. The computer readable program instructions may execute entirely on the user's computer, partly on the user's computer as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus', and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus', or another device to cause a series of operational steps to be performed on the computer, other programmable apparatus or other device to produce a computer implemented process, such that the instructions which execute on the computer, other programmable apparatus', or another device implement the functions/acts specified in the flowchart and/or block diagram block or blocks.

The flowcharts and/or block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or act or carry out combinations of special purpose hardware and computer instructions.

The terminology used herein is for the purpose of describing particular embodiments only and is not intended to limit the invention. As used herein, the singular forms "a", "an" and "the" are intended to include the plural forms as well, unless the context clearly indicates otherwise. It will further be understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or steps plus function elements in the claims below are intended to include any structure, material, or act for performing the function in combination with other claimed elements, as specifically claimed. The description of the present invention has been presented for purposes of illustration and description, but is not intended to be exhaustive or limited to the invention in the form disclosed. Many modifications and variations will be apparent to those of ordinary skills in the art without departing from the scope and spirit of the invention. The embodiments are chosen and described in order to best explain the principles of the invention and the practical application, and to enable others of ordinary skills in the art to understand the invention for various embodiments with various modifications, as are suited to the particular use contemplated.

What is claimed is:

1. A method for extracting information from a molecular pathway diagram, said method comprising:
    providing a molecular pathway diagram,
    detecting basic graphical structural elements in said molecular pathway diagram resulting in a set of basic objects,
    detecting a graphical semantic of each of said basic graphical structural elements resulting in a set of structural primitives,
    detecting a graphical syntax of said basic graphical structural elements relative to each other and to said molecular pathway diagram, and
    assigning metadata to a plurality of said detected basic graphical structural elements resulting in a set of entities and relationships, said metadata comprising data corresponding to the basic graphical structural elements, data corresponding to the graphical semantic of each of said basic graphical structural elements and data corresponding to the graphical syntax.

2. The method according to claim 1, wherein each of said basic graphical structural elements comprises at least one of: a closed shape, a line, a curve, an arrow, or a character.

3. The method according to claim 1, wherein said graphical semantic of each of said basic graphical structural elements comprises data corresponding to at least one of a location, a size, a color or an appearance.

4. The method according to claim 1, wherein detecting said graphical syntax comprises at least one of:
    detecting a relative position of said basic graphical structural elements to each other,
    detecting a distance between a pair of relative positions,
    detecting an inclusion of one of said basic graphical structural elements in another one of said basic graphical structural elements,
    detecting an intersection of one of said basic graphical structural elements with another one of said basic graphical structural elements, or
    detecting a continuity of one of said basic graphical structural elements.

5. The method according to claim 1, wherein a graphical object smaller than a molecular pathway diagram driven threshold value is interpreted as a character.

6. The method according to claim 5, also comprising:
    applying an optical character recognition method to sets of detected characters,
    determining said value of said detected characters, and
    applying a confidence correction to each of said detected characters.

7. The method according to claim 1, said set of structural primitives comprises:
    a text string, a connection node and/or a content node.

8. The method according to claim 2, also comprising:
    applying a modified Voronoi diagram method using said closed shape as starting point for the modified Voronoi diagram method.

9. The method according to claim 1, also comprising applying a cognitive computing model to said entities and relationships.

10. The method according to claim 9, wherein said application of said cognitive computing model comprises at least one of:
    a rule method,
    a decision making method, or
    a reasoning method.

11. A system for extracting information from a molecular pathway diagram, said system comprising:
    at least one processor;
    at least one memory including computer program code, the at least one memory and the computer program code configured to, with the at least one processor, cause the system at least to:
        select a molecular pathway diagram from a storage system,
        detect basic graphical structural elements in said molecular pathway diagram resulting in a set of basic objects,
        detect a graphical semantic of each of said basic graphical structural elements resulting in a set of structural primitives,
        detect a graphical syntax of said basic graphical structural elements relative to each other and to said molecular pathway diagram, and
        assign metadata to a plurality of said detected basic graphical structural elements resulting in a set of entities and relationships, said metadata comprising data corresponding to the basic graphical structural elements, data corresponding to the graphical semantic of each of said basic graphical structural elements and data corresponding to the graphical syntax.

12. The system according to claim 11, wherein each of said basic graphical structural elements comprises at least one of: a closed shape, a line, a curve, an arrow, or a character.

13. The system according to claim 11, wherein said graphical semantic of each of said basic graphical structural elements comprises data corresponding to at least one of: a location, a size, a color, or an appearance.

14. The system according to claim 11, wherein said detection of said graphical syntax
comprises at least one of:
- detection of a relative position of said basic graphical structural elements to each,
- detection of a distance between a pair of relative positions,
- detection of an inclusion of one of said basic graphical structural elements in another one of said basic graphical structural elements,
- detection of an intersection of one of said basic graphical structural elements with another one of said basic graphical structural elements, or
- detection of a continuity of one of said basic graphical structural elements.

15. The system according to claim 11, wherein a graphical object smaller than a molecular pathway diagram driven threshold value is interpreted as a character.

16. The system according to claim 15, wherein the at least one memory and the computer program code are configured to, with the at least one processor, cause the system to:
- apply an optical character recognition method to sets of detected characters, determine said value of said detected characters, and
- apply a confidence correction to a set of said detected characters.

17. The system according to claim 11, wherein said set of structural primitives comprises at least one of: a text string, a connection node, or a content node.

18. The system according to claim 12, wherein the at least one memory and the computer program code are configured to, with the at least one processor, cause the system to:
- apply a modified Voronoi diagram method using said closed shape as starting point.

19. The system according to claim 11, wherein the at least one memory and the computer program code are configured to, with the at least one processor, cause the system to:
- apply a cognitive computing model to said entities and relationships.

20. A computer program product for extracting information from a molecular pathway diagram, said computer program product comprising a computer readable storage medium having program instructions embodied therewith, said program instructions being executable by one or more computing systems to cause said one or more computing systems to:
- provide a molecular pathway diagram,
- detect basic graphical structural elements in said molecular pathway diagram resulting in a set of basic objects,
- detect a graphical semantic of each of said basic graphical structural elements resulting in a set of structural primitives,
- detect a graphical syntax of said basic graphical structural element relative to each other and to said molecular pathway diagram, and
- assign metadata to a plurality of said detected basic graphical structural elements resulting in a set of entities and relationships, said metadata comprising data corresponding to the basic graphical structural elements, data corresponding to the graphical semantic of each of said basic graphical structural elements and data corresponding to the graphical syntax.

* * * * *